(12) United States Patent
Besko et al.

(10) Patent No.: US 10,098,577 B2
(45) Date of Patent: Oct. 16, 2018

(54) TECHNIQUE FOR REMANUFACTURING A MEDICAL SENSOR

(71) Applicant: COVIDIEN LP, Mansfield, MA (US)

(72) Inventors: David P. Besko, Thornton, CO (US); Donald R. Sandmore, Lyons, CO (US)

(73) Assignee: COVIDIEN LP, Mansfield, MA (US)

( * ) Notice: Subject to any disclaimer, the term of this patent is extended or adjusted under 35 U.S.C. 154(b) by 168 days.

(21) Appl. No.: 14/877,671

(22) Filed: Oct. 7, 2015

(65) Prior Publication Data

US 2016/0022184 A1 Jan. 28, 2016

Related U.S. Application Data

(63) Continuation of application No. 13/226,714, filed on Sep. 7, 2011, now Pat. No. 9,161,722.

(51) Int. Cl.
*A61B 5/1455* (2006.01)
*A61B 5/00* (2006.01)
*A61B 5/145* (2006.01)

(52) U.S. Cl.
CPC ...... *A61B 5/14552* (2013.01); *A61B 5/14546* (2013.01); *A61B 5/6832* (2013.01); *A61B 5/6833* (2013.01); *A61B 2560/028* (2013.01); *A61B 2560/0443* (2013.01); *A61B 2560/0475* (2013.01); *A61B 2562/0233* (2013.01); *A61B 2562/0238* (2013.01); *A61B 2562/08* (2013.01); *A61B 2562/12* (2013.01); *A61B 2562/164* (2013.01); *A61B 2562/222* (2013.01); *A61B 2562/242* (2013.01); *Y10T 29/4973* (2015.01)

(58) Field of Classification Search
None
See application file for complete search history.

(56) References Cited

U.S. PATENT DOCUMENTS

| | | | |
|---|---|---|---|
| 4,964,408 | A | 10/1990 | Hink et al. |
| 5,090,410 | A | 2/1992 | Saper et al. |
| 5,170,786 | A | 12/1992 | Thomas et al. |
| 5,209,230 | A | 5/1993 | Swedlow et al. |
| 5,337,744 | A | 8/1994 | Branigan |
| 5,452,717 | A | 9/1995 | Branigan et al. |
| 5,660,567 | A | 8/1997 | Nierlich et al. |
| 5,673,693 | A | 10/1997 | Solenberger |
| 5,697,367 | A | 12/1997 | Lewis et al. |

(Continued)

FOREIGN PATENT DOCUMENTS

| | | |
|---|---|---|
| AU | 2120892 A1 | 4/1993 |
| EP | 1945099 | 7/2008 |

(Continued)

*Primary Examiner* — Eric Winakur
*Assistant Examiner* — Marjan Fardanesh
(74) *Attorney, Agent, or Firm* — Fletcher Yoder P.C.

(57) ABSTRACT

Remanufactured medical sensors and methods for remanufacturing used medical sensors are provided. Such a remanufactured sensor may include certain components from a used medical sensor and certain new components. For example, a remanufactured regional oximetry sensor may include a padding layer, an emitter and a pair of detectors, a flexible circuit coupled to the emitter and detectors, and a patient-contacting adhesive layer. The flexible circuit, the emitter, the first detector, the second detector, or any combination thereof, are from a used medical sensor, and the padding layer, the patient-contacting adhesive layer, or a combination thereof, are new.

15 Claims, 9 Drawing Sheets

(56) References Cited

U.S. PATENT DOCUMENTS

| | | |
|---|---|---|
| 5,797,841 A | 8/1998 | Delonzor et al. |
| 5,810,724 A | 9/1998 | Gronvall |
| RE36,000 E | 12/1998 | Swedlow et al. |
| 5,851,178 A | 12/1998 | Aronow |
| 5,891,026 A | 4/1999 | Wang et al. |
| 5,910,108 A | 6/1999 | Solenberger |
| 5,919,133 A | 7/1999 | Taylor et al. |
| 5,999,834 A | 12/1999 | Wang et al. |
| 6,073,038 A | 6/2000 | Wang et al. |
| 6,144,868 A | 11/2000 | Parker |
| 6,149,481 A | 11/2000 | Wang et al. |
| 6,173,196 B1 | 1/2001 | Delonzor et al. |
| 6,253,098 B1 | 6/2001 | Walker et al. |
| 6,256,523 B1 | 7/2001 | Diab et al. |
| 6,321,100 B1 | 11/2001 | Parker |
| 6,343,224 B1 | 1/2002 | Parker |
| 6,377,829 B1 | 4/2002 | Al-Ali |
| 6,430,423 B2 | 8/2002 | Delonzor et al. |
| 6,519,487 B1 | 2/2003 | Parker |
| 6,671,531 B2 | 12/2003 | Al-Ali et al. |
| 6,675,031 B1 | 1/2004 | Porges et al. |
| 6,678,543 B2 | 1/2004 | Diab et al. |
| 6,681,126 B2 | 1/2004 | Solenberger |
| 6,684,091 B2 | 1/2004 | Parker |
| 6,725,075 B2 | 4/2004 | Al-Ali |
| 6,735,459 B2 | 5/2004 | Parker |
| 6,745,061 B1 | 6/2004 | Hicks et al. |
| 6,748,254 B2 | 6/2004 | O'Neil et al. |
| 6,763,255 B2 | 7/2004 | Delonzor et al. |
| 6,792,300 B1 | 9/2004 | Diab et al. |
| 6,813,511 B2 | 11/2004 | Diab et al. |
| 6,920,345 B2 | 7/2005 | Al-Ali et al. |
| 6,950,687 B2 | 9/2005 | Al-Ali |
| 7,039,449 B2 | 5/2006 | Al-Ali |
| 7,048,687 B1 | 5/2006 | Reuss et al. |
| 7,190,984 B1 | 3/2007 | Delonzor et al. |
| 7,225,007 B2 | 5/2007 | Al-Ali et al. |
| 7,245,953 B1 | 7/2007 | Parker |
| 7,248,910 B2 | 7/2007 | Li et al. |
| 7,272,425 B2 | 9/2007 | Al-Ali |
| 7,321,790 B2 | 1/2008 | Delonzor et al. |
| 7,369,886 B2 | 5/2008 | Delonzor et al. |
| 7,373,188 B2 | 5/2008 | Delonzor et al. |
| 7,373,189 B2 | 5/2008 | Delonzor et al. |
| 7,373,190 B2 | 5/2008 | Delonzor et al. |
| 7,373,191 B2 | 5/2008 | Delonzor et al. |
| 7,386,334 B2 | 6/2008 | Delonzor et al. |
| 7,389,130 B2 | 6/2008 | Delonzor et al. |
| 7,418,284 B2 | 8/2008 | Delonzor et al. |
| 7,440,788 B2 | 10/2008 | Jenkins et al. |
| 7,561,905 B2 | 7/2009 | Delonzor et al. |
| 7,684,842 B2 | 3/2010 | Ollerdessen |
| 2003/0109775 A1 | 6/2003 | O'Neil et al. |
| 2003/0171662 A1 | 9/2003 | O'Connor et al. |
| 2004/0133088 A1 | 7/2004 | Al-Ali |
| 2004/0147822 A1 | 7/2004 | Al-Ali et al. |
| 2005/0043600 A1 | 2/2005 | Diab et al. |
| 2006/0161054 A1 | 7/2006 | Reuss et al. |
| 2006/0200018 A1 | 9/2006 | Al-Ali |
| 2007/0021659 A1 | 1/2007 | Delonzor et al. |
| 2007/0021660 A1 | 1/2007 | Delonzor et al. |
| 2007/0021662 A1 | 1/2007 | Delonzor et al. |
| 2007/0027378 A1 | 2/2007 | Delonzor et al. |
| 2007/0027379 A1 | 2/2007 | Delonzor et al. |
| 2007/0027380 A1 | 2/2007 | Delonzor et al. |
| 2007/0078311 A1 | 4/2007 | Al-Ali et al. |
| 2007/0123763 A1 | 5/2007 | Al-Ali et al. |
| 2007/0244378 A1 | 10/2007 | Al-Ali et al. |
| 2008/0009691 A1 | 1/2008 | Parker |
| 2008/0033267 A1 | 2/2008 | Al-Ali |
| 2008/0081971 A1 | 4/2008 | Ollerdessen |
| 2008/0088467 A1 | 4/2008 | Al-Ali |
| 2008/0091089 A1 | 4/2008 | Guillory et al. |
| 2008/0091090 A1 | 4/2008 | Guilloiy et al. |
| 2008/0208023 A1 | 8/2008 | Gruvac et al. |
| 2008/0228053 A1 | 9/2008 | Wang et al. |
| 2009/0259114 A1 | 10/2009 | Johnson et al. |
| 2009/0323267 A1 | 12/2009 | Besko et al. |
| 2010/0076282 A1 | 3/2010 | Sandmore |
| 2010/0081902 A1 | 4/2010 | McKenna et al. |
| 2010/0249554 A1 | 9/2010 | McKenna et al. |
| 2010/0249557 A1 | 9/2010 | Besko et al. |
| 2010/0331638 A1 | 12/2010 | Besko et al. |
| 2012/0071739 A1 | 3/2012 | Chen et al. |
| 2012/0071742 A1 | 3/2012 | Medina et al. |
| 2012/0136223 A1 | 5/2012 | Hodge et al. |
| 2012/0136257 A1 | 5/2012 | Krishnan et al. |
| 2012/0216335 A1 | 8/2012 | McKenna et al. |
| 2012/0253148 A1 | 10/2012 | Haisley et al. |
| 2012/0253152 A1 | 10/2012 | Haisley et al. |
| 2012/0253159 A1 | 10/2012 | Medina et al. |

FOREIGN PATENT DOCUMENTS

| | | |
|---|---|---|
| JP | 27195816 A2 | 8/2007 |
| WO | WO06092624 A1 | 9/2006 |

TECHNIQUE FOR REMANUFACTURING A MEDICAL SENSOR

CROSS-REFERENCE TO RELATED APPLICATIONS

This application is a continuation of U.S. application Ser. No. 13/226,714, filed Sep. 7, 2011, the disclosure of which is hereby incorporated in its entirety for all purposes.

BACKGROUND

The present disclosure relates generally to remanufacturing disposable medical sensors and, more particularly, to remanufacturing, i.e., reconstructing, used medical sensors.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

A wide variety of devices have been developed for non-invasively monitoring physiological characteristics of patients. For example, a pulse oximetry sensor system may non-invasively detect various patient blood flood characteristics, such as the blood-oxygen saturation of hemoglobin in arterial blood, the volume of individual blood pulsations supply the tissue, and/or the rate of blood pulsations corresponding to each heart beat of a patient. During operation, the pulse oximeter sensor emits light and photoelectrically senses the absorption and/or scattering of the light after passage through the perfused tissue. A photo-plethysmographic waveform, which corresponds to the cyclic attenuation of optical energy through the patient's tissue, may be generated from the detected light. Additionally, one or more physiological characteristics may be calculated based upon the amount of light absorbed or scattered. More specifically, the light passed through the tissue may be selected to be of one or more wavelengths that may be absorbed or scattered by the blood in an amount correlative to the amount of the blood constituent present in the blood. The amount of light absorbed and/or scattered may then be used to estimate the amount of blood constituent in the tissue using various algorithms.

For example, a reflectance-type sensor placed on a patient's forehead may emit light into the site and detect the light that is "reflected" back after being transmitted through the forehead region. A transmission-type sensor having a bandage configuration may be placed on a finger, wherein the light waves are emitted through and detected on the opposite side of the finger. In either case, the amount of light detected may provide information that corresponds to valuable physiological patient data. The data collected by the sensor may be used to calculate one or more of the above physiological characteristics based upon the absorption or scattering of the light. For instance, the emitted light is typically selected to be of one or more wavelengths that are absorbed or scattered in an amount related to the presence of oxygenated versus de-oxygenated hemoglobin in the blood. The amount of light absorbed and/or scattered may be used to estimate the amount of the oxygen in the tissue using various algorithms.

The sensors generally include one or more emitters that emit the light and one or more detectors that detect the light. During use, the emitter and detector may be held against the patient's skin to facilitate the transmission of light through the skin of the patient. Because these sensors come into contact with patient tissues, and possibly fluids, they are either sanitized for re-use or they are discarded after use. Indeed, many pulse oximeter medical sensors may be disposable and originally intended for use on a single patient. However, even disposable sensors often include relatively expensive components that may be reused if the sensor could be refurbished.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

Figure 1:
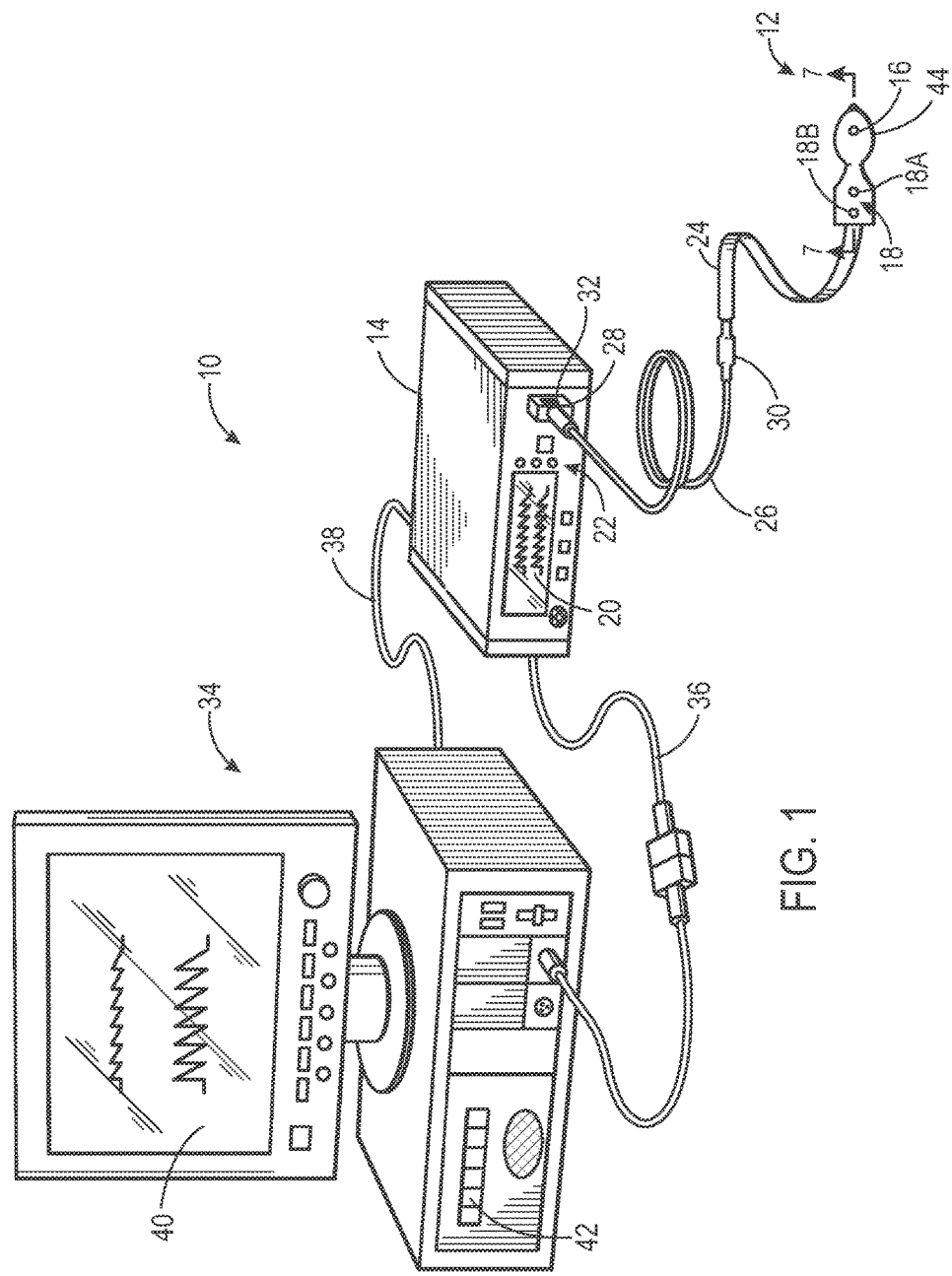
FIG. 1 is a front view of an embodiment of a monitoring system configured to be used with a sensor for oximetry and regional saturation, in accordance with an aspect of the present disclosure.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," and "the" are intended to mean that there are one or more of the elements. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features. Also, as used herein, the term "over" or "above" refers to a component location on a sensor that is closer to patient tissue when the sensor is applied to the patient.

As noted above, the present embodiments relate to remanufacturing sensors that may be used to determine regional oxygen saturation. For example, the sensors described herein may incorporate one or more emitters and one or more detectors for determining the level of blood oxygen saturation in a particular region, such as a cerebral or somatic region. The sensors described herein may be constructed using a combination of new materials (i.e., materials that have not been incorporated into a medical sensor) and components taken from one or more used sensors. For example, a sensor may include a plurality of padding (e.g., foam, sponge, gel, or fiber) layers disposed on either side of a flexible electronic circuit, and an adhesive layer for attaching to a patient, such as to the patient's forehead, stomach, back, or another somatic region. Sensors constructed using the remanufacturing techniques described herein may incorporate used padding layers, flexible circuits, emitters, detectors, and, in certain embodiments, used adhesive layers, or any combination thereof.

By way of example, an INVOS® cerebral/somatic sensor, such as an OxyAlert™ NIR sensor or a SomaSensor® by Somanetics Corporation, which may include one or more emitters and a pair of detectors for determining site-specific oxygen levels, represents such sensors. Moreover, other types of sensors, such as those used for measuring water fraction, hematocrit, bispectral index (BIS), etc., may benefit from the techniques disclosed herein as well. An example system incorporating a sensor capable of performing regional oximetry is discussed with respect to FIG. 1, with various features of the sensor, such as a flexible circuit, foam layers, adhesive layers, and connector being discussed with respect to FIGS. 2, 7, and 11. As noted above, these sensors are generally known to be one-time-use medical sensors that may be disposed after use by one patient. Though disposable, some components of these used sensors, such as the cables, connectors, and memory units associated therewith, may be employed in the construction of remanufactured sensors. Reusing these components to reconstruct a sensor may reduce waste, consequently reducing an impact on the environment, while accordingly reducing costs. Example methods for remanufacturing these and other sensors from new and/or used components are discussed with respect to FIGS. 3-6, 8-10, 12, and 13.

With this in mind, FIG. 1 depicts an embodiment of a patient monitoring system 10 that may be used in conjunction with a medical sensor 12. Although the depicted embodiments relate to sensors for use on a patient's head, it should be understood that, in certain embodiments, the features of the sensor 12 as provided herein may be incorporated into sensors for use on other tissue locations, such as the back, the stomach, the heel, the ear, an arm, a leg, or any other appropriate measurement site. In addition, although the embodiment of the patient monitoring system 10 illustrated in FIG. 1 relates to photoplethysmography or pulse oximetry, the system 10 may be configured to obtain a variety of medical measurements with a suitable medical sensor. For example, the system 10 may additionally be configured to determine patient electroencephalography (e.g., a bispectral index), or any other desired physiological parameter such as water fraction or hematocrit.

As noted, the system 10 includes the sensor 12 that is communicatively coupled to a patient monitor 14. The illustrated sensor 12 includes an emitter 16 and a pair of detectors 18. The emitter 16 and detectors 18 of the sensor 12 are coupled to the monitor 14 via first and second cables 24, 26 through a connector 28 coupled to a sensor port of the monitor 14. The first cable 24 may interface directly with the sensor 12 and may include a relatively flat, flexible cable having a plurality of printed conductors on a dielectric substrate. The first cable 24 may provide enhanced comfort for a patient due to its soft feel and flexibility, which may enable the patient to move about freely. However, other cables having a plurality of conductors (e.g., wires) may be directly coupled to the sensor 12 in other embodiments. For example, in certain embodiments, a cable such as the second cable 26 may couple directly to the sensor 12. The materials of the first cable 24 are discussed in detail with respect to FIG. 2. The first cable 24 may couple to the second cable 26, which may include a plurality of conductors disposed within an insulating material, via a cable adapter 30. As illustrated, the second cable 26 couples to the monitor 14 via the connector 28. It should be noted that in some embodiments, however, the sensor 12 and associated cables 24, 26 may couple to a pre-amplifier (not shown) configured to amplify signals collected by the detectors 18. For example, the pre-amplifier may have a cable that couples to the second cable 26 and additional cable that couples to the monitor 14. However, in the illustrated embodiment, the pre-amplifier may be provided as a part of the monitor 14. The connector 28, in certain embodiments, may include a memory unit 32 that may be configured to store patient historical data, such as historical regional oximetry data. The memory unit 32, alternatively or additionally, may be configured to store sensor-related information and time-out functionality to facilitate the operability of the sensor 12 with the monitor 14. In some embodiments, the memory unit 32 may be an erasable programmable read-only memory (EPROM) having code configured to execute a time-out routine that disables the operability of the sensor 12 with the monitor 14 after a predetermined number of connections and/or uses, or after a predetermined amount of time.

The monitor 14 includes a monitor display 20 configured to display information regarding the physiological parameters monitored by the sensor 12, information about the system, and/or alarm indications. The monitor 14 may include various input components 22, such as knobs, switches, keys and keypads, buttons, etc., to provide for operation and configuration of the monitor. The monitor 14 also includes a processor that may be used to execute code such as code for implementing various monitoring functionalities enabled by the sensor 12. As discussed below, for example, the monitor 14 may be configured to process signals generated by the detectors 18 to estimate the amount of oxygenated vs. de-oxygenated hemoglobin in a monitored region of the patient.

The monitor 14 may be any suitable monitor, such as a pulse oximetry monitor available from Nellcor Puritan Bennett LLC or an INVOS® System monitor available from Somanetics Corporation. Furthermore, to upgrade conventional operation provided by the monitor 14 to provide additional functions, the monitor 14 may be coupled to a multi-parameter patient monitor 34 via a cable 36 connected to a sensor input port or via a cable 38 connected to a digital communication port. In addition to the monitor 14, or alternatively, the multi-parameter patient monitor 34 may be configured to calculate physiological parameters and to provide a central display 40 for the visualization of information from the monitor 14 and from other medical monitoring devices or systems. The multi-parameter monitor 34 includes a processor that may be configured to execute code. The multi-parameter monitor 34 may also include various input components 42, such as knobs, switches, keys and keypads, buttons, etc., to provide for operation and configuration of the a multi-parameter monitor 34. In addition, the monitor 14 and/or the multi-parameter monitor 34 may be connected to a network to enable the sharing of information with servers or other workstations.

The sensor 12, illustrated as operatively connected to the monitor 14, may include a sensor body 44 that houses the emitter 16 for emitting light at certain wavelengths into a tissue of a patient and the detectors 18 for detecting the light after it is reflected and/or absorbed by the blood and/or tissue of the patient. The sensor body 44 may be formed from any suitable material, including rigid or conformable materials, such as fabric, paper, rubber or elastomeric compositions (including acrylic elastomers, polyimide, silicones, silicone rubber, celluloid, PMDS elastomer, polyurethane, polypropylene, acrylics, nitrile, PVC films, acetates, and latex). One embodiment is discussed in detail below with respect to FIG. 2.

In certain embodiments, the sensor 12 may be a wireless sensor 12. Accordingly, the wireless sensor 12 may establish a wireless communication with the patient monitor 14 and/or the multi-parameter patient monitor 34 using any suitable wireless standard. By way of example, the wireless module may be capable of communicating using one or more of the ZigBee standard, WirelessHART standard, Bluetooth standard, IEEE 802.11x standards, or MiWi standard.

Figure 2:
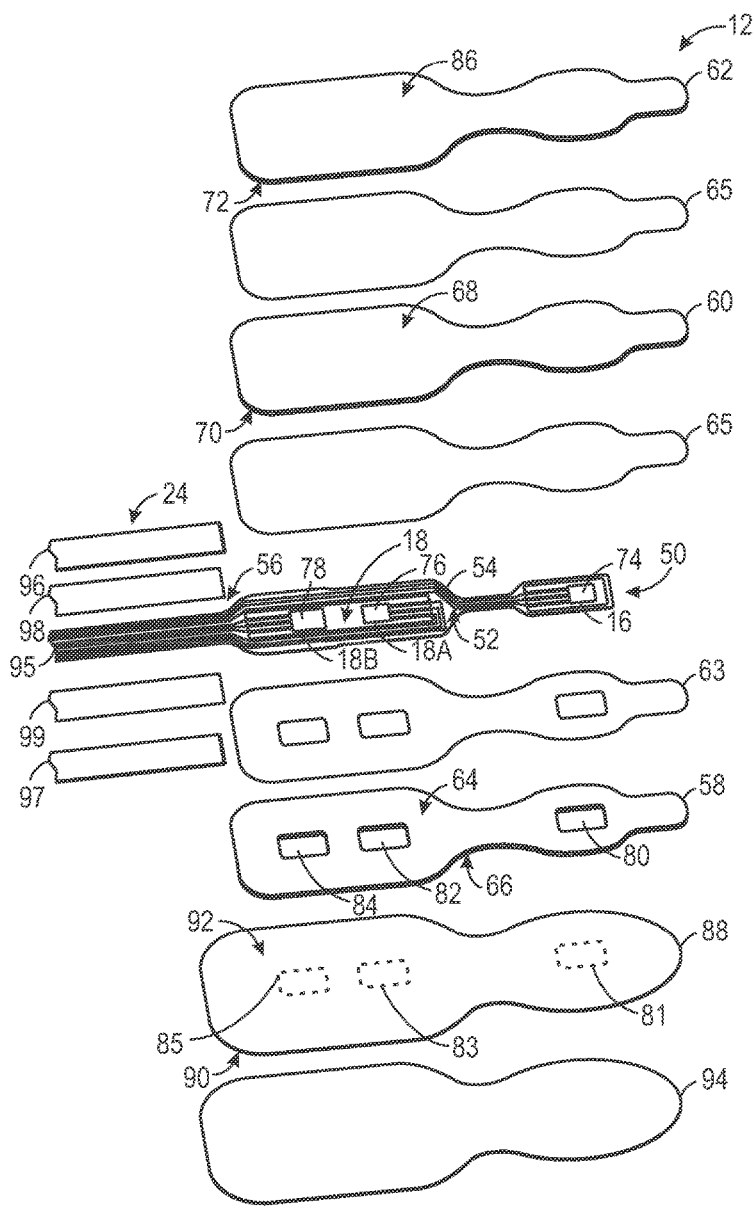
FIG. 2 is an exploded perspective view of an embodiment of the sensor of FIG. 1, in accordance with an aspect of the present disclosure.

As provided herein, the sensor 12 may be configured to perform regional oximetry. Indeed, in one embodiment, the sensor 12 may be an INVOS® cerebral/somatic sensor available from Somanetics Corporation. In regional oximetry, by comparing the relative intensities of light received at two or more detectors, it is possible to estimate the blood oxygen saturation of hemoglobin in a region of a body. For example, a regional oximeter may include a sensor to be placed on a patient's forehead and may be used to calculate the oxygen saturation of a patient's blood within the venous, arterial and capillary systems of a region underlying the patient's forehead (e.g., in the cerebral cortex). As illustrated in FIGS. 1 and 2, the sensor 12 may include the emitter 16 and the two detectors 18: one detector 18A that is relatively "close" to the emitter 16 and another detector 18B that is relatively "far" from the emitter 16. Light intensity of one or more wavelengths may be received at both the "close" and the "far" detectors. Thus, the detector 18A may receive a first portion of light and the detector 18B may receive a second portion of light. Each of the detectors 18 may generate signals indicative of their respective portions of light. For example, the resulting signals may be contrasted to arrive at a regional saturation value that pertains to additional tissue through which the light received at the "far" detector passed (tissue in addition to the tissue through which the light received by the "close" detector passed, e.g., the brain tissue) when it was transmitted through a region of a patient (e.g., a patient's cranium). Surface data from the skin and skull is subtracted out to produce an $rSO_2$ value for deeper tissues.

To provide conformance to these or other patient tissues that are monitored by the sensor 12, the sensor 12 may include a flexible (flex) circuit 50 operatively connected to the emitter 16 and the detectors 18, as illustrated in FIG. 2. FIG. 2 depicts one embodiment of the manner in which the flex circuit 50 may be integrated into various used and/or new components to form the sensor 12. Thus, in certain embodiments, the sensor 12 of FIG. 2 may be a remanufactured sensor constructed from a combination of new and used sensor materials. In this way, various materials forming the sensor 12 of FIGS. 1 and 2 discussed herein may be new or from a used medical sensor (e.g., a used regional oximeter). As illustrated, the emitter 16 and the detectors 18 are operatively connected to the flex circuit 50. The flex circuit 50 may include various features for providing power to and carrying signals to and from the emitter 16 and the detectors 18, such as a plurality of conductors 52 disposed (e.g., printed) on a main flexible substrate 54. The main flexible substrate 54 may include any suitable flexible dielectric substrate. For example, the main flexible substrate 54 may include organic polymers such as polyimides, one example of which is KAPTON® polyimide film available from DuPont™. The plurality of conductors 52 may be formed from any suitable conductive material, such as gold (Au), silver (Ag), copper (Cu), or any combination thereof. The conductors 52 may be disposed on the main flexible substrate 54 using any suitable technique known in the art, such as photolithographic methods. As illustrated, the conductors 52 lead into a tapered section 56 of the flexible circuit 50, where they become a part of the first cable 24.

In FIG. 2, the flexible circuit 50 is disposed between a plurality of laminated layers including an inner foam layer 58 (i.e., between the flexible circuit 50 and the patient) and first and second outer foam layers 60, 62. It should be noted that while the present embodiments are discussed in the context of including foam layers, any suitable padding materials may be used in accordance with the disclosed embodiments. Therefore, as discussed herein, other medically-suitable padding materials that are compressible and capable of providing a degree of cushioning may be used in place of the foam layers. By way of example, padding materials may generally include foam, sponge, gel cushioning, fiber (e.g., woven fiber), or the like. Indeed, in certain of the remanufacturing embodiments discussed below, such as when any one or a combination of the foam layers 58, 60, 62 may be replaced, it may be desirable to use the same or different padding materials in the remanufactured version of the sensor 12.

Generally, the foam layers 58, 60, 62 may be provided to protect the emitter 16 and the detectors 18 from damage, and also to enhance patient comfort. Thus, any number of padding layers may be suitably provided depending on the desired end use of the sensor 12. Indeed, in certain embodiments, such as in embodiments where the sensor 12 may be used on an adult or in certain pediatric uses, the sensor 12 may not include the inner foam layer 58. For example, in the SAFB-SM disposable adult SOMASENSOR® or the SPFB disposable pediatric SOMASENSOR®, the inner foam layer 58 may not be present. Each of the foam layers 58, 60, 62 may include any natural or synthetic foam material that is suitable for medical applications, such as medical-grade urethane foam. As an example, the foam layers 58, 60, 62 may include PORON® urethane foam available from Rogers Corporation.

To adhere the foam layers 58, 60, 62 to one another, and, in the case of the inner foam layer 58 and the first outer foam layer 60, to the flexible circuit 50, an adhesive may be provided on or between each layer. For example, in the illustrated embodiment, an adhesive 63 (e.g., an adhesive layer) may be applied directly to a top surface 64 and, in some embodiments, a bottom surface 66 of the inner foam layer 58. Similarly, as illustrated, one or more adhesives, such as an adhesive 65, may be applied to the top and/or bottom surfaces 68, 70 of the first outer foam layer 60, and to a bottom surface 72 of the second outer foam layer 62. The adhesives 63, 65 used for each of the surfaces 64, 66, 68, 70, 72 may be the same or different, and may include any suitable adhesive capable of securing the foam layers to one another and/or to the flexible circuit 50. For example, the adhesives 63, 65 may be an acrylic adhesive that is applied to each surface, a supported or unsupported transfer tape layer disposed on and/or between the surfaces, or any similar adhesive material applied directly to and/or between each of the surfaces 64, 66, 68, 70, 72. The adhesives 63, 65 may also be configured to block the ingress of light and other interfering signals into the sensor 12.

For example, in certain embodiments, any one or a combination of the surfaces 64, 66, 68, 70, 72 may be coated with a layer or backing that includes a conductive adhesive, for example to shield the flexible circuit 50, the emitter 16, the detectors 18, or any combination thereof from light and/or other electromagnetic interference (EMI). Indeed, the conductive adhesive may be colored (e.g., black) so as to filter all or a portion of light entering into the sensor 12, and the conductive portions of the adhesive may act as a Faraday shield to dissipate EMI from the sensor 12. Conductive adhesive materials employed in the construction and/or remanufacturing embodiments described herein may include intrinsically conductive polymers that are adhesive, nonconductive polymers that are adhesive, or any combination thereof. As an example, the adhesive material of the conductive adhesive may include a pressure-sensitive adhesive such as an acrylic adhesive. The intrinsically conductive polymers and non-conductive polymers may be combined with other conductive materials, such as metallic foil backing (e.g., copper foil backing), conductive fillers (e.g., conductive particles, tubes, rods, or fibers), and the like. By way of example, any one or a combination of the surfaces 64, 66, 68, 70, 72 may be coated with an ARCARE® electrically conductive adhesive available from Adhesives Research, Inc of Glen Rock, Pa. In certain embodiments, the conductive adhesives may also shield the flexible circuit 50, the emitter 16, the detectors 18, or any combination thereof, from patient noise. Thus, it should be noted that in any of the remanufacturing methods described herein, any of the surfaces 64, 66, 68, 70, 72 may be remanufactured to include these conductive adhesives, and in embodiments where any of the surfaces 64, 66, 68, 70, 72 have these conductive adhesives, the conductive adhesive may be replenished or otherwise replaced as appropriate.

As noted above, the flexible circuit 50 is disposed between the inner foam layer 58 and the first outer foam layer 60, which are also attached to each other at the extents surrounding the flexible circuit 50. However, as noted above, in other embodiments, the inner foam layer 58 may not be present. In the illustrated embodiment, the flexible circuit 50 is secured to the top surface 64 of the inner foam layer 58 and the bottom surface 70 of the first outer foam layer 60, and the portion of these surfaces 64, 70 that are not attached to the flexible circuit 50 are attached to one another. The inner foam layer 58, which is disposed between an active face 74 of the emitter 16, an active face 76 of the "close" detector 18A, an active face 78 of the "far" detector 18B, and the patient tissue to be monitored, includes a first optical window 80, a second optical window 82, and a third optical window 84. The first optical window 80 enables the active face 76 of the emitter 16 to transmit unimpeded light toward the patient tissue, and the second and third optical windows 82, 84 enable the active faces 76, 78, respectively, of the detectors 18 to receive the transmitted light from the patient (i.e., respective first and second portions of light). It should be noted that while the illustrated embodiment depicts the inner foam layer 58 as having the optical windows 80, 82, 84, the inner foam layer 58 may not have the optical windows, such as in embodiments where the inner foam layer 58 and any adhesive secured thereto does not absorb or scatter the wavelengths of light used by the emitter 16 and the detectors 18. In such embodiments, the sensor 12 may include an opaque perimeter material to prevent the ingress of light into the sensor 12. Further, an opaque material may be provided between the emitter 16 and the detectors 18 to prevent an optical shunt from occurring between the emitter 16 and detectors 18.

Conversely, the first and second outer foam layers 60, 62 may be configured to prevent the ingress of light, which may interfere with oximetry measurements, into the sensor 12. Indeed, an opaque paint, thin polymeric layer, or similar covering may be applied to a top surface 86 of the second outer foam layer 62 to prevent the ingress of light into the sensor 12. Moreover, because the top surface 86 of the second outer foam layer 62 may be the outermost layer of the sensor 12, various indications may be provided thereon, such as decorative markings, placement instructions, trade names, indications for use (e.g., indications for adult or neonate use), and so forth.

The opposite side of the sensor 12 (i.e., the patient side) includes a patient-contacting adhesive layer 88 laminated on the bottom surface 66 of the inner foam layer 58 in some embodiments, and laminated on the flexible circuit 50 or the adhesive 63 in other embodiments. The patient-contacting adhesive layer 88 may include any adhesive material suitable for integration into medical devices (e.g., a hypoallergenic adhesive material). In some embodiments, the adhesive material may be substantially transparent with respect to the wavelengths of light used for the oximetry measurements performed by the sensor 12. In other embodiments where the patient-contacting adhesive layer 88 is not transparent with respect to the wavelengths of light used for the oximetry measurements, the patient-contacting adhesive layer 88 may include first, second, and third optical windows 81, 83, 85 (e.g., openings), illustrated as dashed lines, corresponding to the respective positions of the emitter 16 and the first and second detectors 18A, 18B. By way of example, the patient-contacting adhesive layer 88 may include an acrylic adhesive or a hydrocolloid adhesive. Generally, hydrocolloid adhesives may provide enhanced comfort for the patient and avoid damage to the patient's skin when the sensor 12 is removed or repositioned. Further, the patient-contacting adhesive layer 88 may be a transfer adhesive or may be a single-sided adhesive. Thus, a patient-contacting surface 90 of the patient-contacting adhesive layer 88 will generally be provided as an adhesive surface, but a top surface 92 of the patient-contacting adhesive layer 88 may or may not be adhesive, depending on whether the bottom surface 66 of the inner foam layer 58 is adhesive or if the adhesive 63 is provided. Generally, the patient-contacting adhesive layer 88 may be a transfer adhesive where the patient-contacting surface 90 and the top surface 92 are both adhesive. In embodiments where the patient-contacting adhesive layer 88 is a hydrocolloid layer, both surfaces 90, 92 may be adhesive. In certain embodiments, the surface area of the hydrocolloid adhesive may be greater than the surface area of the foam layers (e.g., layer 58), which may leave an outer perimeter of the adhesive surface 92 exposed once the sensor 12 is assembled. Accordingly, a film or other non-adhesive material may be applied to the surface 92 to render it non-adhesive. Indeed, it may be desirable to render the surface 92 non-adhesive because the exposed portion of the surface 92, once the sensor 12 is assembled and in use, may undesirably adhere to clothing or other contaminants. Accordingly, in embodiments where the patient-contacting adhesive layer 88 includes a hydrocolloid layer, the non-adhesive film or coating may be used to render all or a portion of the surface 92 non-adhesive during remanufacture.

A release liner 94 may also be provided to prevent the inadvertent attachment of the patient-contacting layer 88 to a surface before the intended use of the sensor 12. The release liner may include any liner having a release material suitable for use with the patient-contacting adhesive layer 88, such as a coated release paper or a release plastic film. Example release materials include polyolefins (e.g., polypropylene, high- and low-density polyethylene), polyesters (e.g., biaxially-oriented polyethylene terephthalate), polyvinyl alcohol, Kraft paper, polystyrene, or the like.

As illustrated, the flexible circuit 50 tapers into a tail region 95, which may serve as the inner portion of the first cable 24. However, in other embodiments the flexible circuit 50 may not taper into a cable, and may instead directly interface with a cable, such as the second cable 26. The tail region 95 may be surrounded by a padding material, such as first and second foam wrap layers 96, 97. As an example, the first and second foam wrap layers 96, 97 may include a polyethylene foam, and may adhere to the tail region 95 via first and second adhesives 98, 99. Because the first and second foam wrap layers 96, 97 are exposed and may encounter patient tissue and fluids or otherwise become contaminated, they may be remanufactured in accordance with the disclosed techniques.

Figure 4:
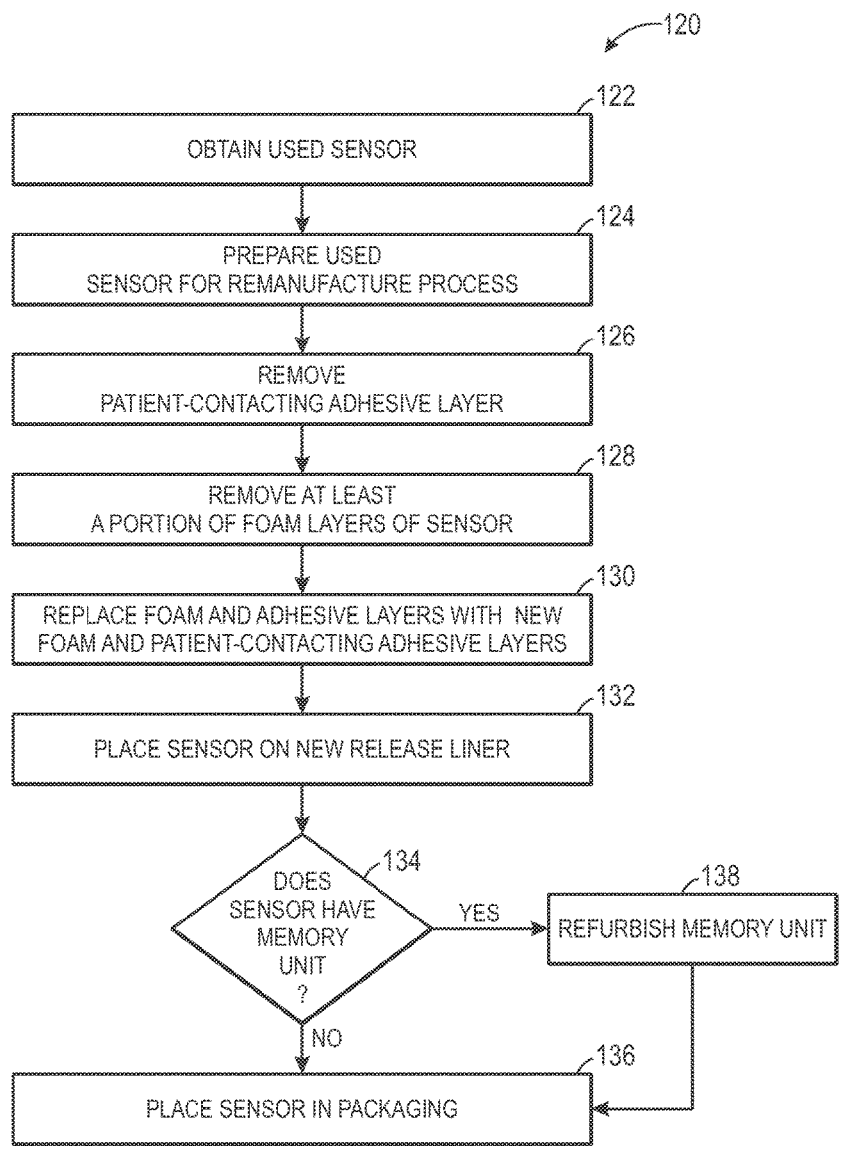
FIG. 4 is a process flow diagram of an embodiment of a method for remanufacturing the sensor of FIG. 1 including removing at least a portion of one or more foam layers and the patient-contacting adhesive layer of the sensor, in accordance with an aspect of the present disclosure.
Figure 5:
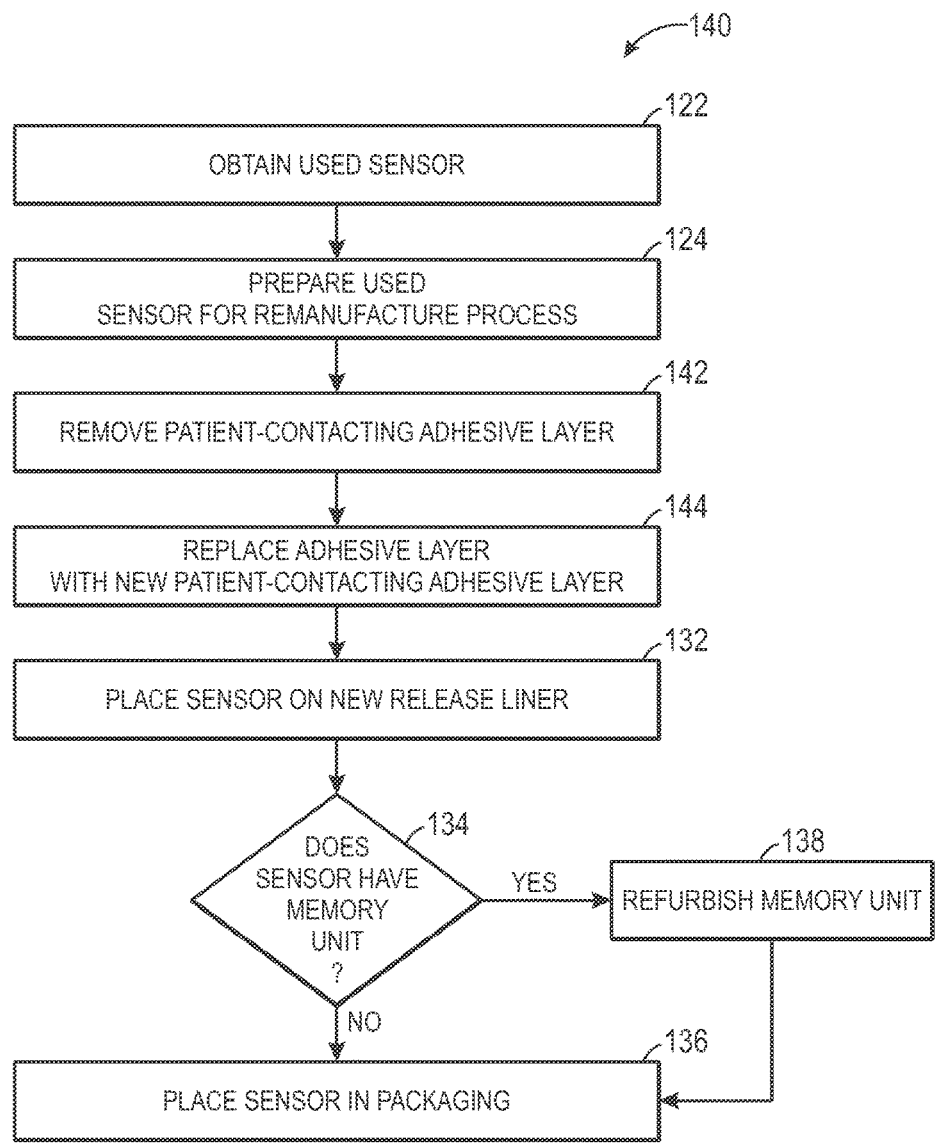
FIG. 5 is a process flow diagram of an embodiment of a method for remanufacturing the sensor of FIG. 1 including replacing the patient-contacting adhesive layer of the sensor, in accordance with an aspect of the present disclosure.
Figure 6:
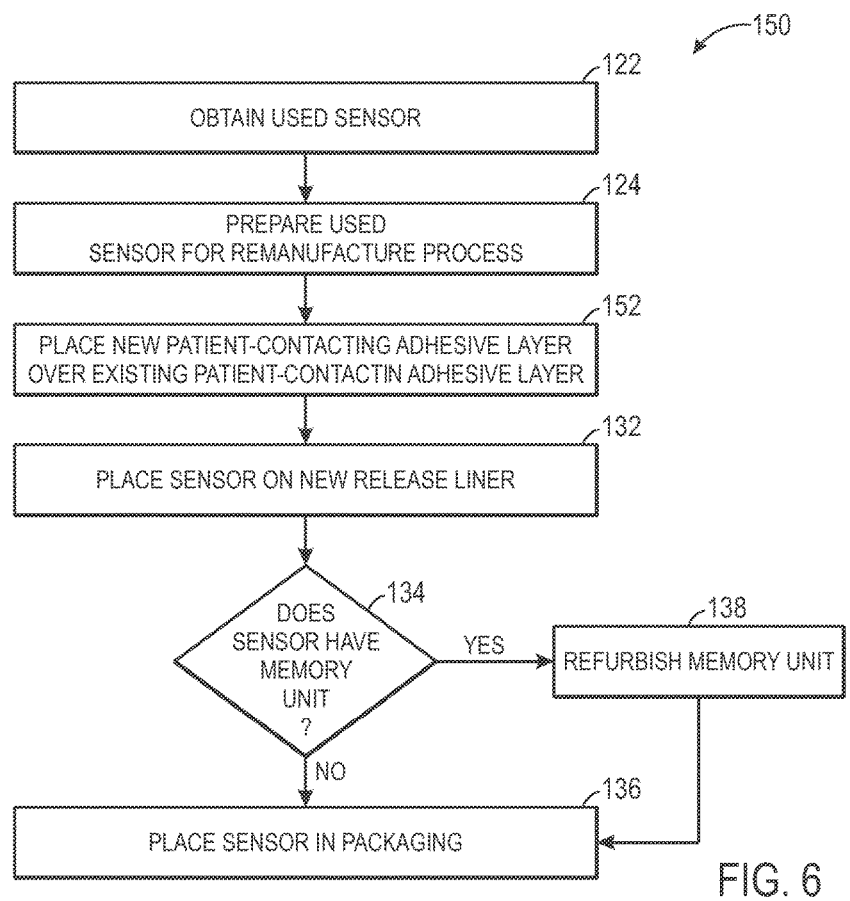
FIG. 6 is a process flow diagram of an embodiment of a method for remanufacturing the sensor of FIG. 1 including placing a new patient-contacting adhesive layer over the used patient-contacting adhesive layer of the sensor, in accordance with an aspect of the present disclosure.

As noted above, the sensor 12 discussed with respect to FIGS. 1 and 2 may be manufactured from a combination of new, refurbished, and/or used materials. Indeed, the present embodiments provide various methods for remanufacturing regional oximetry sensors in accordance with the embodiments discussed above. For example, FIG. 3 illustrates a generalized sensor remanufacturing method, FIGS. 4-6 illustrate sensor remanufacturing methods for replacing and/or refurbishing various features of the sensor 12, and FIGS. 8-10 and 12 each illustrate a connector/memory unit remanufacturing method that can be performed in conjunction with or independently of the methods of FIGS. 4-6.

Figure 3:
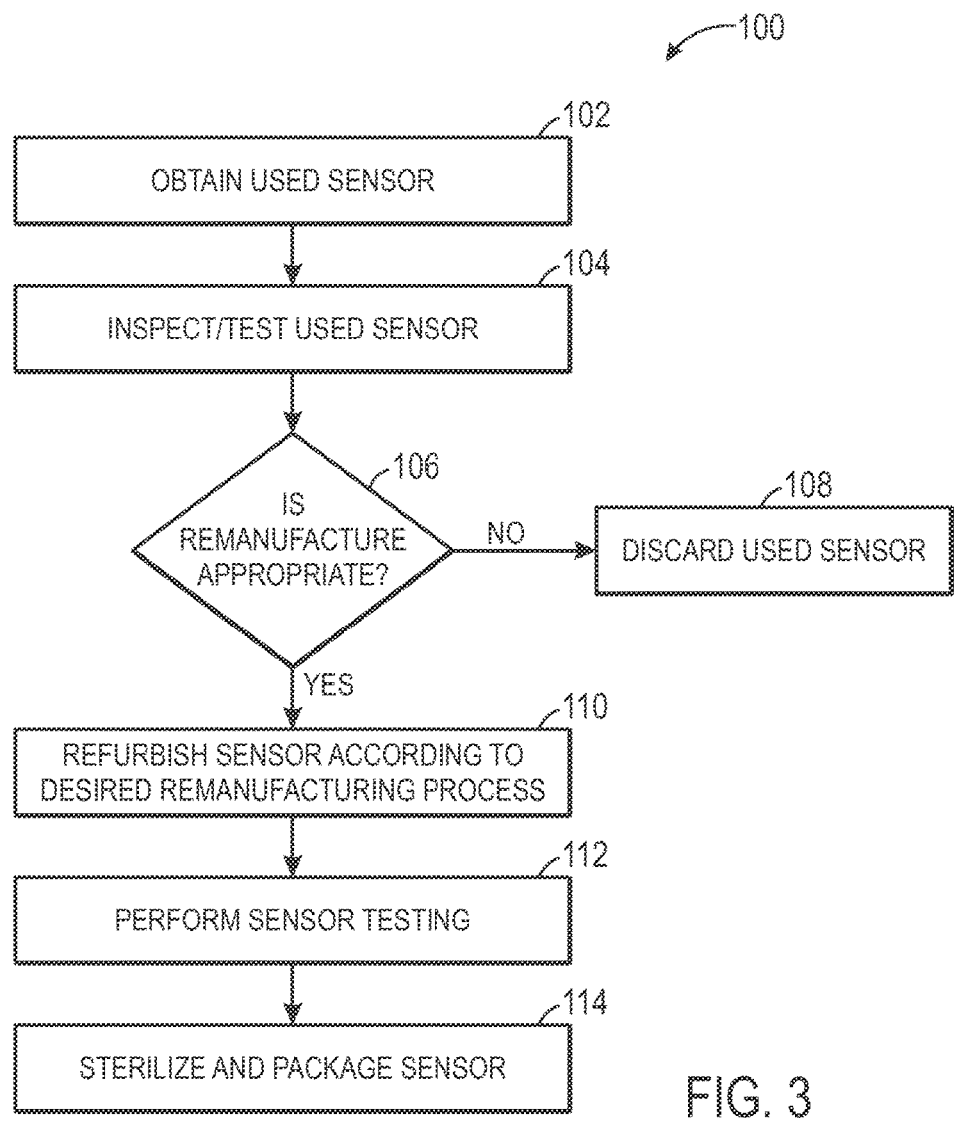
FIG. 3 is a process flow diagram of an embodiment of a general method for remanufacturing the sensor of FIG. 1, in accordance with an aspect of the present disclosure.

Referring now to FIG. 3, an embodiment of a method 100 for remanufacturing a medical sensor (e.g., an INVOS® sensor), such as the sensor 12, is illustrated. The method begins with obtaining a used version of the sensor 12 (block 102). The used version of the sensor 12 may be a single-use medical sensor (i.e., for use on a single patient) or may be a reusable sensor. The sensor 12 may be obtained, as an example, by a technician or similar manufacturing personnel. The sensor 12 may be sterilized before or after the acts represented by block 102 such that the sensor 12 is suitable for handling by a technician or similar worker. The sensor 12 may also undergo inspection and/or testing to determine the operability of the sensor 12 (block 104). As an example, in embodiments where the sensor 12 is a pulse oximetry sensor, the testing may include testing the operation and accuracy of the emitter(s) 16, the detector(s) 18, the sensor cable 24, the cable connector 28, and any other electronic features of the sensor 12, such as the memory unit 32.

After the sensor 12 has been inspected and tested, it may be determined whether it is appropriate to remanufacture the sensor (query 106). For example, it may be determined whether the sensor 12 includes suitable components for remanufacture (e.g., by reviewing the results of the sensor testing acts of block 104 and/or visual inspection). Alternatively or additionally, it may be determined whether the sensor 12 has undergone previous iterations of remanufacturing. Accordingly, the sensor 12 may include one or more indications as to whether the sensor 12 has been previously remanufactured, such an external mark on the sensor 12 or a counter stored on the memory unit 32.

In embodiments where remanufacture is not appropriate, the used version of the sensor 12 may be discarded (block 108). For example, one or more features of the used version of the sensor 12 may be inoperative, such as the emitter 16 and detectors 18 (e.g., FIG. 2), the cable 24, and so on. Depending on the degree to which the sensor 12 may be inoperative, it may no longer be cost-effective to remanufacture, and the sensor 12 may be discarded. In other embodiments, as mentioned above, the sensor 12 may have an external mark or a stored counter that indicates that the sensor 12 is not suitable for remanufacture. Indeed, as discussed herein, the external markings and/or the counter on the memory unit 32 may be incremented with each remanufacturing procedure.

Conversely, in embodiments where it is determined that at least a portion of the sensor 12 is suitable for remanufacturing, the sensor 12 may be remanufactured according to certain remanufacturing processes (block 110). For example, in embodiments where the sensor 12 includes at least some operable components (e.g., an operable emitter and/or detector), or has one or more indications via the memory unit 32 and/or external marks that remanufacturing is suitable, the sensor 12 may be remanufactured. Embodiments of certain remanufacturing processes are discussed below. Indeed, while the remanufacturing processes discussed below are presented in the context of replacing all or a part of the sensor body 44, connector 28, memory unit 32, or a combination, it should be noted that the processes described below may be performed independently or in conjunction with other steps, such as replacing the emitter 16 and/or the detectors 18.

After the sensor 12 has been remanufactured, the sensor 12 is then tested to ensure that it is within certain operational tolerances (block 112). For example, the sensor 12 may be attached or otherwise coupled to a test rig, which may determine and, if suitable, adjust varying operational parameters of the sensor 12. For example, various sensor-specific information may be stored on the memory unit 32, such as light emitting diode (LED)-related calibration data if the emitter 16 and/or detectors 18 are replaced, information pertaining to the sensor 12 (e.g., the name of the sensor 12, a model code for the sensor 12), or the like. The sensor 12 may then be packaged and sterilized (block 114), and sent to a medical facility for use.

Certain sensor remanufacturing processes that may be performed in conjunction with or independent of the method 100 set forth above may include replacing some of all of the foam and/or adhesive layers of the sensor 12 (FIG. 2) with new foam and/or adhesive layers. FIG. 4 depicts an embodiment of one such method 120. The method 120 begins with obtaining the used version of the sensor 12 (block 122), which may include receiving the sensor 12 from a testing facility (e.g., in embodiments where method 120 is performed in conjunction with method 100), or obtaining the used sensor from a medical facility (e.g., in embodiments where method 120 is not performed in conjunction with method 100). For example, the sensor 12 may be obtained after the sensing components have been tested, or after the sensor 12 has been used to monitor a patient.

After the sensor 12 is obtained, the sensor 12 may be prepared for remanufacturing (block 124). For example, the preparation may include cleaning the sensor 12, such as by removing debris or other material away from the optics of the sensor 12, and may also include sterilizing the sensor 12. For example, the acts according to block 124 may include sterilizing the sensor 12 using ethylene oxide (EtO) gas, gamma irradiation, autoclaving, Pasteurization, chemical antiseptics, or other such materials and methods. Sterilization may be performed at the same facility as other remanufacturing steps, or may be performed at a separate facility.

Once the sensor has been prepared for remanufacturing, the patient-contacting adhesive layer (e.g., layer 88 of FIG. 2) may be removed (block 126). Specifically, the patient-contacting adhesive layer 88 may be removed before removing any of the foam layers 58, 60, 62, after removing the foam layers 58, 60, 62, or as the foam layers 58, 60, 62 are removed, as discussed below. Referring to the embodiment illustrated in FIG. 2 for example, as the inner foam layer 58 is removed, the patient-contacting adhesive layer 88, which is laminated against the inner foam layer 58, may also be removed. Further, it should be noted that in embodiments where the sensor 12 does not include the inner foam layer 58, removing the patient-contacting adhesive layer 88 may expose at least a portion of the flexible circuit 50 for remanufacture.

At least a portion of the foam layers 58, 60, 62 and/or the foam wrap layers 96, 97 may be removed from the sensor 12 (block 128). For example, referring to the embodiment illustrated in FIG. 2, all or a portion of the second outer foam layer 62, the first outer foam layer 60, the inner foam layer 58, the first foam wrap layer 96, the second foam wrap layer 97, or any combination thereof, may be partially or completely removed by cutting or pulling all or a portion of each layer away from the flexible circuit 50/tail region 95. It will be appreciated that during removal, the adhesives associated with each layer may also be removed. For example, it may be desirable to remove the second outer foam layer 62 and the first and second foam wrap layers 96, 97 due to their increased level of exposure to the environment during use. Accordingly, adhesives 65, 98, 99 may also be removed. In embodiments where the inner foam layer 58 is present, it may be desirable to remove the inner foam layer 58 and associated adhesive 63 to expose at least a portion of the flexible circuit 50 or due to its proximity to patient tissue. Furthermore, any one or a combination of the foam layers may be shaved (e.g., along its length) to expose a clean foam surface that can be attached to a new or used foam or adhesive layer. In embodiments where the sensor 12 does not include the inner foam layer 58, no foam layers may be removed from the body 44 of the sensor 12.

Once the foam 58, 60, 62, 96, 97 and adhesive layers 63, 65, 88, 98, 99 have been removed as appropriate, they may be replaced with new foam 58, 60, 62, 96, 97 and adhesive 63, 65, 88, 98, 99 (block 130). Indeed, any one or a combination of the inner foam layer 58, first outer foam layer 60, and second outer foam layer 62 may be replaced along with the patient-contacting adhesive layer 88. The foam layers 58, 60, 62, 96, 97 may be replaced with the same or different foam materials than those originally used, and the patient-contacting adhesive layer 88 may be replaced with the same or a different adhesive. For example, the patient-contacting adhesive layer 88 may originally (i.e., before remanufacture) include an acrylic adhesive, and may be replaced with a hydrocolloid layer. Conversely, a hydrocolloid patient-contacting adhesive layer 88 may be replaced with an acrylic adhesive layer, or any suitable adhesive layer.

After the new foam layers 58, 60, 62, 96, 97 and new adhesive layers 63, 65, 88, 98, 99 have been integrated into the remanufactured version of the sensor 12, the sensor 12 may be placed on a new release liner 94 (block 132). The new release liner 94 may include any liner having a release material suitable for use with the patient-contacting adhesive layer 88, such as a coated release paper or a release plastic film. Example release materials include polyolefins (e.g., polypropylene, high- and low-density polyethylene), polyesters (e.g., biaxially-oriented polyethylene terephthalate), polyvinyl alcohol, Kraft paper, polystyrene or the like.

Before, during, or after the steps described above, it may be determined whether the used sensor has a memory unit (e.g., a memory unit having a time-out feature) (query 134). For example, a technician may inspect the connector 28 (FIG. 2) to identify whether the connector 28 houses a memory unit, or this may be done automatically during testing. The connector 28 may include markings, a particular shape, a color code, or similar feature to indicate the presence of a memory unit. In embodiments where the sensor 12 does not include a memory unit, the sensor 12 may be packaged (block 136). However, in embodiments where the sensor 12 does include a memory unit, the memory unit 32 (block 138) may be refurbished before packaging the sensor 12. For example, the memory unit 32 may be cleared of historical and/or programming data, may be re-programmed, may be cleaned, or a combination. In some embodiments, the memory unit 32 may be replaced. However, because the connector 28 and associated memory unit 32 may represent a signification portion of the overall cost for each sensor 12, it may be desirable to retain the connector 28 and memory unit 32 and simply re-program the memory unit 32. Accordingly, the acts represented by block 138 may include re-programming the memory unit 32. Certain embodiments of the manner in which the acts represented by block 138 may be performed are discussed in further detail below with respect to FIGS. 8-10 and 12.

While the method 120 described above may be performed in situations where it is desirable to replace one or more of the foam layers 58, 60, 62 of the sensor 12, it may be desirable to retain the foam layers 58, 60, 62 and only replace the patient-contacting adhesive layer 88 of the sensor 12. For example, during inspection (e.g., in method 100) to determine whether the sensor 12 should be remanufactured, it may be determined that the foam layers 58, 60, 62 do not need replacing. Accordingly, FIG. 5 depicts an embodiment of a method 140 that includes replacing the patient-contacting adhesive layer 88 while retaining the used foam layers 58, 60, 62. It will be appreciated that method 140 may include certain steps that are similar or the same steps as those described above with respect to method 120. Accordingly, those steps are referenced using the same reference numerals throughout the remainder of the present disclosure where the steps are the same. As with method 120, method 140 includes obtaining the used version of the sensor 12 (block 122). For example, the sensor 12 may be obtained from a sterilization facility, a third party that collects the used sensors 12, or directly from the medical facility. The sensor 12 may also be prepared for the remanufacturing process (block 124) by performing sterilization, re-painting used cables and/or outer layers, as discussed above.

After the sensor 12 has been suitably prepared, the patient-contacting adhesive layer 88 may be removed without removing any foam layers 58, 60, 62 (block 142). For example, referring to the embodiment illustrated in FIG. 2, the patient-contacting adhesive layer 88 may be pulled and/or cut away from the bottom surface 66 of the inner foam layer 58. The used patient-contacting adhesive layer 88 may then be replaced with a new patient-contacting adhesive layer 88 (block 144). For example, as set forth above with respect to certain of the acts represented by block 130, the patient-contacting adhesive layer 88 may originally (i.e., before remanufacture) include an acrylic adhesive, and may be replaced with a hydrocolloid layer. Conversely, a hydrocolloid-containing patient-contacting adhesive layer 88 may be replaced with an acrylic adhesive layer, or any suitable adhesive layer. Further, the patient-contacting adhesive layer 88 may simply be replaced with the same type of adhesive layer.

After the adhesive layer has been replaced, the sensor may be placed on a new release liner (block 132). It may also be determined whether the sensor has a memory unit (query 134). As set forth above, in embodiments where the sensor 12 does not have the memory unit 32, the sensor 12 may be placed in its packaging (block 136). Conversely, in embodiments where the sensor 12 does include the memory unit 32, the memory unit 32 may be refurbished before the sensor is placed in its packaging (block 138), as discussed above.

Although the patient-contacting adhesive layer 88 is removed in the methods 120, 140 described above, in certain embodiments, it may be desirable to place a new patient-contacting adhesive layer 88 over the used patient-contacting adhesive layer 88. For example, referring to the embodiment illustrated in FIG. 2, removal of the used patient-contacting adhesive layer 88 may cause at least a portion of the inner foam layer 58 to be removed. Such situations may be undesirable, as the beneficial cushioning and protection for the flexible circuit 50, as well as the enhanced patient comfort provided by the inner foam layer 58, may be disrupted. Accordingly, the present disclosure also provides a method 150, illustrated in FIG. 6, for remanufacturing the sensor 12 by placing a new patient-contacting adhesive layer 88 over the used patient-contacting adhesive layer 88.

Figure 7:
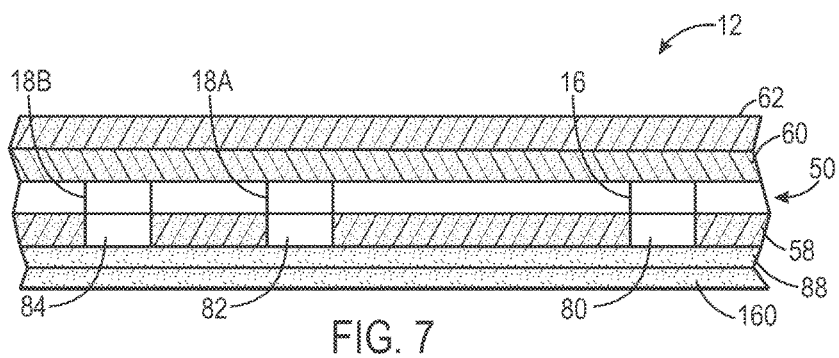
FIG. 7 is a cross-sectional view taken along section 7-7 of FIG. 1 and illustrating an embodiment of the sensor of FIG. 1 having a new patient-contacting adhesive layer disposed over the used patient-contacting adhesive layer of the sensor, in accordance with an aspect of the present disclosure.

The method 150 includes obtaining the used version of the sensor 12 (block 122) and preparing the used version of the sensor 12 for remanufacturing (block 124), as described above with respect to methods 120 and 140. In method 150, the preparation of the sensor 12 may include trimming away a portion of the used patient-contacting adhesive layer 88 to fit within the extents of a new adhesive layer. Thereafter, the new patient-contacting adhesive layer 88 may be placed on top of the used patient-contacting adhesive layer 88 (block 152). Again, the new patient-contacting adhesive layer 88 may be the same or different than the used patient-contacting adhesive layer 88. Thus, a cross-section taken along line 7-7 of the sensor 12, an embodiment of which is illustrated in FIG. 7, may reveal two distinct patient-contacting layers: the used patient-contacting adhesive layer 88 and a new patient-contacting adhesive layer 160 disposed over the used patient-contacting adhesive layer 88. However, it should be noted that in certain embodiments, there may be no discernable difference between the used patient-contacting adhesive layer 88 and the new patient-contacting adhesive layer 160, such as in configurations where the adhesive layers 88, 160 are the same, or where one or both include an unsupported transfer tape layer.

Returning to the method 150 illustrated in FIG. 6, after the new patient-contacting adhesive layer has been laminated over the used patient-contacting adhesive layer, the acts represented by blocks 132-138, as described above, may be performed. Thus, the sensor may be placed on a new release liner (block 132). It may also be determined whether the sensor 12 has the memory unit 32 (query 134). In embodiments where the sensor 12 does not have the memory unit 32, the sensor 12 may be placed in its packaging (block 136). Conversely, in embodiments where the sensor 12 does include the memory unit 32, the memory unit 32 may be refurbished before the sensor 12 is placed in its packaging (block 138) as discussed above.

Figure 8:
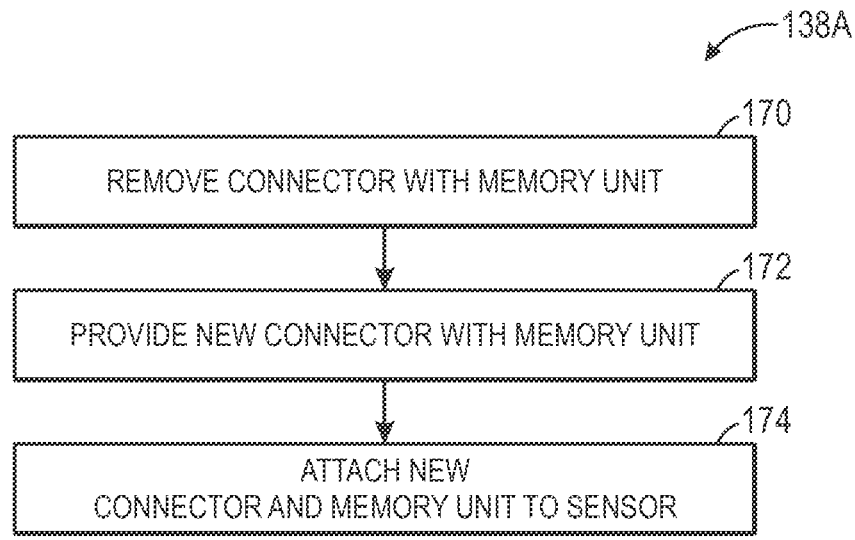
FIG. 8 is a process flow diagram of an embodiment of a method for refurbishing the time-out feature in accordance with the methods of FIGS. 3-6, including replacing the connector of the sensor of FIG. 1, in accordance with an aspect of the present disclosure.

As noted above, FIGS. 8-10 and 12 illustrate embodiments of methods for refurbishing the memory unit 32 of the sensor 12. Specifically, FIG. 8 illustrates a method 138A that includes replacing the used connector 28 having the memory unit 32 with a new connector 28 having a new memory unit 32. Specifically, method 138A includes removing the connector 28, which houses the memory unit 32, from the sensor 12 (block 170). For example, referring to the embodiment illustrated in FIG. 1, the connector 28 may be removed from the second sensor cable 26, the connector 28 and the second sensor cable 26 may be removed from the first sensor cable 24, or the connector 28, the second sensor cable 26, and the first sensor cable 24 may be removed from the sensor 12. Because the first sensor cable 24 may be integral with the flexible circuit 50 (FIG. 2), in certain embodiments it may be desirable to only remove the connector 28 or the connector 28 and the second sensor cable 26.

Once the connector 28 and associated memory unit 32 have been detached from the sensor 12, a new connector 28 having the new memory unit 32 may be provided (block 172). The connector 28 and/or new memory unit 32 may have the same or a similar configuration compared to the used memory unit 32. In some embodiments, the new memory unit 32 may include stored code that enables new or enhanced functionality for the sensor 12 (e.g., when connected to the monitor 14), such as increased patient history functionality and/or updated operational information that reflects any updates, upgrades, or other changes that have been made to the sensor 12. For example, in embodiments where the emitter 16 and/or detectors 18 are replaced, new calibration data may be written to the memory unit 32. The new connector 28 and memory unit 32 may then be attached to the sensor 12 (block 174).

Figure 9:
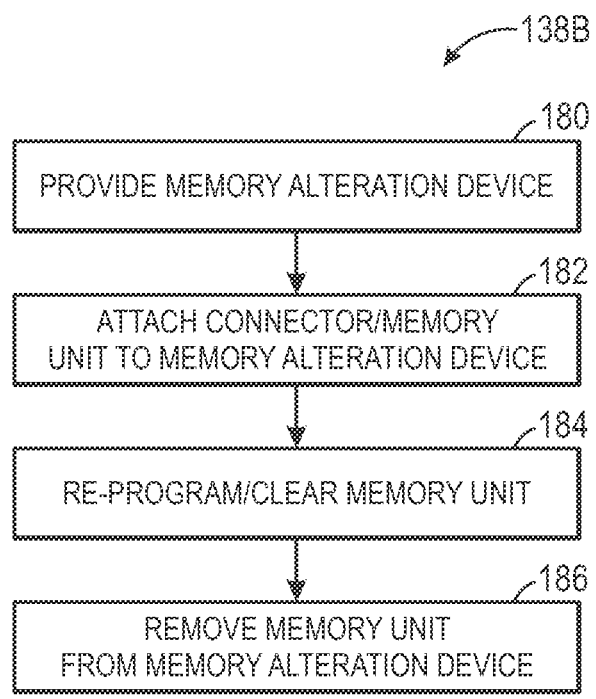
FIG. 9 is a process flow diagram of an embodiment of a method for refurbishing the time-out feature in accordance with the methods of FIGS. 3-6, including re-programming the time-out feature contained within the connector of the sensor of FIG. 1, in accordance with an aspect of the present disclosure.

Because the connector 28 and associated memory unit 32 may represent a signification portion of the overall cost for each sensor 12, it may be desirable to retain the connector 28 and memory unit 32 and simply re-program the memory unit 32. FIG. 9 illustrates an embodiment of a method 138B for re-programming the memory unit 32. The method 138B includes providing a memory alteration device (not shown) (block 180), which may include a computer or other processor-based device that is capable of accessing and deleting at least a portion of the data stored on the memory unit. Indeed, the memory alteration device may be an application-specific or a general-purpose computer having code configured to re-program the memory unit contained within the connector. Furthermore, the memory alteration device may include one or more ports for coupling to the connector or to the memory unit, or both.

After the memory alteration device is provided, the connector 28 and/or memory unit 32 may be coupled to the alteration device (block 182). As noted above, the memory alteration device may include a port that couples to the connector 28 through which the memory alteration device is able to access and re-program the memory unit 32. Alternatively or additionally, the memory alteration device may include a port that specifically receives the memory unit 32, such that the memory unit 32 may be removed from the connector 28 and coupled directly to the memory alteration device for re-programming.

Once the memory unit 32 is directly or indirectly coupled to the memory alteration device, the memory unit 32 may be cleared or otherwise re-programmed (block 184). For example, in embodiments where the memory unit 32 has time-out functionality that causes the sensor to become non-functional after a given number of connections, uses, or after a certain amount of time in operation, the memory alteration device may re-set the number of connections, uses, or time in operation to zero or another lower threshold value. Alternatively or additionally, in embodiments where the memory unit 32 contains stored patient or other historical data, the memory alteration device may clear the historical data. As noted above, in embodiments where the emitter 16 and/or the detectors 18 are replaced, new or updated calibration data may be written to the memory unit 32. In certain embodiments, sensor-related information may be written to the memory unit 32, which may be displayed on the display of a monitor to which the sensor 12 may attach (e.g., the display 20 of the patient monitor 14). For example, the memory unit 32 may be programmed such that the type of sensor is displayed (e.g., the name or model number of the sensor). An indication that the sensor 12 has been remanufactured, and in some embodiments, the number of remanufacturing iterations that the sensor 12 has undergone, may be provided along with the type of sensor. The indication may include, by way of example, a combination of alphanumeric characters or a combination of ASCII characters, or both. For example, for a disposable adult SomaSensor® from Somanetics Corporation (e.g., model SAFB-SM), the display 20 may read "SAFB-SM-R2," with "SAFB-SM" indicating the model of the sensor 12 and "-R2" indicating that the sensor 12 is a sensor that has been remanufactured twice.

Figure 10:
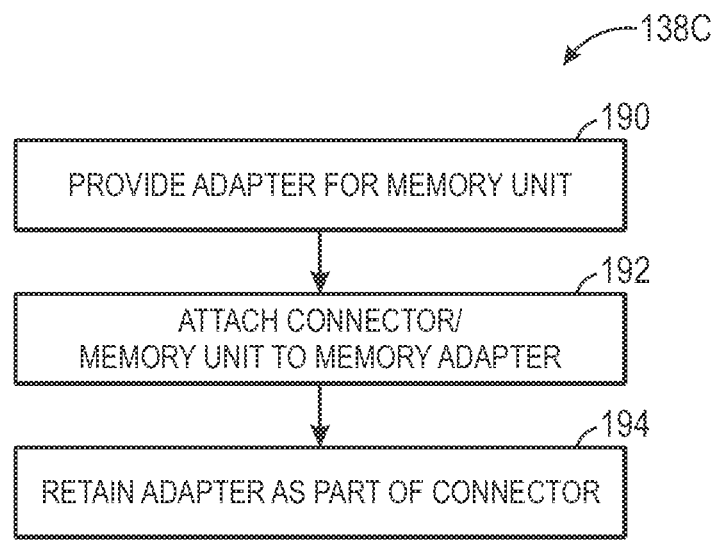
FIG. 10 is a process flow diagram of an embodiment of a method for refurbishing the time-out feature in accordance with the methods of FIGS. 3-6, including providing an adaptor for the time-out feature contained within the connector of the sensor of FIG. 1, in accordance with an aspect of the present disclosure.

After the memory unit 32 is cleared and/or re-programmed, the memory unit 32 may be removed from the memory alteration device (block 186) and may be suitable for use in conjunction with a remanufactured sensor (i.e., sensor 12). However, rather than re-programming or replacing the memory unit 32 as set forth above, it may be desirable to use an adapter that is configured to manipulate a data stream to and/or from the memory unit 32 to enable continued operation of the sensor 12, even after a predetermined number of connections, uses, and/or time has been exceeded. FIG. 10 illustrates an embodiment of a method 138C that includes providing an adapter for the memory unit 32 (block 190). For example, referring to the embodiment depicted in FIG. 1, the adapter may be attached to the connector 28 (block 192). The adapter may be configured to manipulate data transmitted to the memory unit 32 such that the memory unit 32 receives data indicative of a reduced number of connections, a reduced operation time, and/or a reduced number of uses. Alternatively or additionally, the adapter may manipulate data transmitted from the memory unit 32 to the monitor 14 such that the memory unit 32 transmits data indicative of a reduced number of connections, a reduced operation time, and/or a reduced number of uses to the monitor 14. In either scenario, the adapter may enable the continued use, and therefore the retention, of the electronic components of the sensor 12 after remanufacturing, including the flexible circuit 50, the emitter 16, and the detectors 18.

Figure 11:
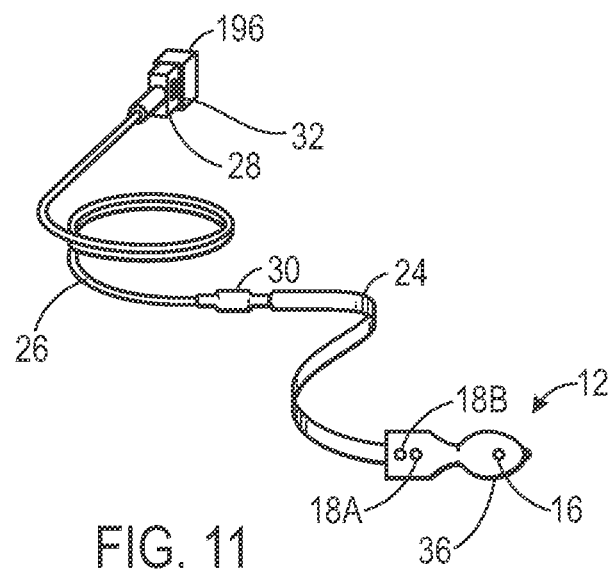
FIG. 11 is a front view of an embodiment of a sensor resulting from the process of FIG. 10, wherein the sensor includes an adapter coupled to the connector for altering the operability of the time-out feature, in accordance with an aspect of the present disclosure.

Due to its mode of operation, the adapter may be retained as a part of, or integral with, the connector 28 (block 194). An embodiment of such a configuration is illustrated in FIG. 11. Specifically, FIG. 11 depicts an embodiment of the sensor 12 where the connector 28 having the memory unit 32 is connected to an adapter unit 196. In some embodiments, as set forth above, the memory unit 32 may include time-out functionality, which causes the sensor 12 to become inactive after the sensor 12 has been in operation after a predetermined amount of time. As noted, because the connector 28, memory unit 32, and other electrical components of the sensor 12 may be retained in the manufacturing process, it may be desirable to increase the amount of time that these components may be placed in operation. Thus, the adapter unit 196 may be configured to disable or otherwise manipulate the time-out functionality to enable the continued use of the sensor 12. For example, the adapter unit 196 may provide data to the memory unit 32 that is indicative of a reduced amount of use compared to the actual amount of use of the sensor 12. Alternatively or additionally, the adapter unit 196 may manipulate the data that is transmitted from the memory unit 32 to the monitor 14 (FIG. 1) to enable the continued use of the sensor 12. Thus, the adapter unit 196, as illustrated, may be coupled to the connector 28 and may have the same or a similar pin-out configuration to the connector 28 for coupling to the monitor 14.

Figure 12:
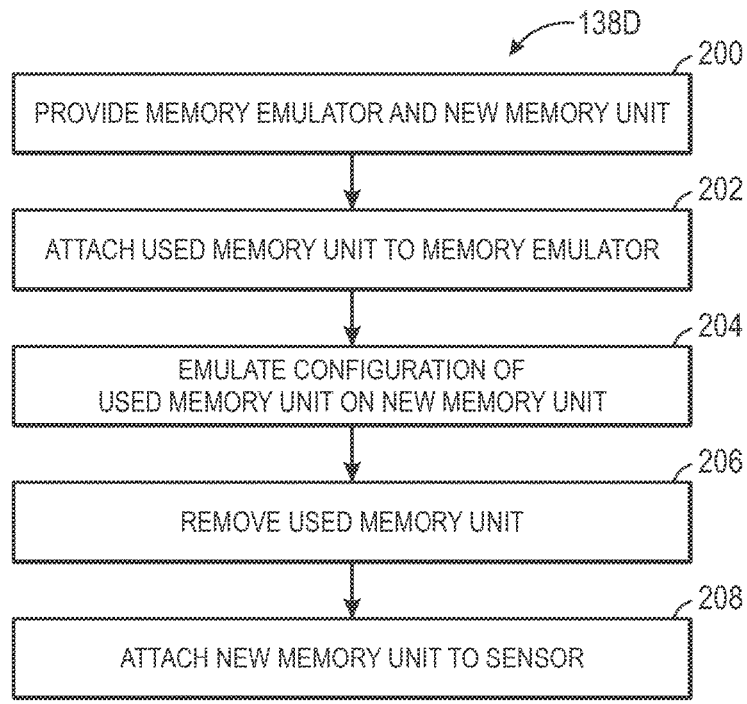
FIG. 12 is a process flow diagram of an embodiment of a method for refurbishing the time-out feature in accordance with the methods of FIGS. 3-6, including emulating the time-out feature contained within the connector of the sensor of FIG. 1 on a new memory unit, in accordance with an aspect of the present disclosure.

While the embodiments described above relate to situations where the original memory unit 32 or original memory unit programming is available, in situations where the memory unit components and/or the programming are not available, it may be desirable to emulate the original memory unit 32. For example, it may be desirable to emulate the original memory unit 32 using a replacement memory unit that has been programmed to mimic the function of the original memory unit. FIG. 12 illustrates an embodiment of such a method 138D, which may be performed in conjunction with certain of the sensor remanufacturing methods described above, or may be performed independently.

The method 138D includes providing a memory emulator (not shown) and a replacement memory unit 32 (block 200). For example, a memory emulator may include an application-specific or general purpose processor-based device (e.g., a computer) that is configured to interface with the original memory unit 32 and/or the connector 28 that includes the memory unit 32. The new memory unit 32 may include a memory device that is capable of being programmed in a similar manner to the original memory unit 32, such as an EPROM. The replacement or new memory unit 32 may also interface with the memory emulator such that the new memory unit 32 may be suitably programmed by the memory emulator to mimic the output of the original memory unit 32.

The used memory unit 32, or the used connector 28 having the memory unit 32, may then be attached to the memory emulator (block 202). For example, the memory emulator may have a connection port that is similar to the connection port of the monitor 14 of FIG. 1. In other embodiments, the memory emulator may include a memory interface, such that the used memory unit 32 is removed from the connector 28 before coupling to the memory emulator.

Once the used memory unit 32 is directly or indirectly connected to the memory emulator, the memory emulator may attempt to automatically, or in conjunction with a technician, emulate the operation of the used memory unit 32. For example, the output of the used memory unit 32 may be analyzed, and the memory emulator may attempt to mimic or otherwise simulate the output of the used memory unit 32. Once the memory emulator has produced one or more routines that are able to suitably match the output of the used memory unit 32, the new memory unit 32 may be programmed to emulate the configuration of the used memory unit 32 (block 204).

After the operation of the used memory unit 32 is suitably emulated, the used memory unit 32 may be removed from the used/remanufactured sensor 12 (block 206). For example, the memory unit 32 may be removed from the connector 28, or the connector 28 may be removed from the sensor 12. In embodiments where the memory unit 32 has already been removed from the connector 28 during the emulation process, the connector 28 may be removed from the sensor 12. Indeed, once the used memory unit 32 has been removed, the new memory unit 32, which emulates the operation of the used memory unit 32, may be attached to the sensor 12 (block 208). For example, in embodiments where the used memory unit 32 has been removed from the connector 28, the new memory unit 32 may be integrated into the connector 28. However, in embodiments where the used connector 28 has been removed, a new connector 28 may be provided that includes the new memory unit 32.

Figure 13:
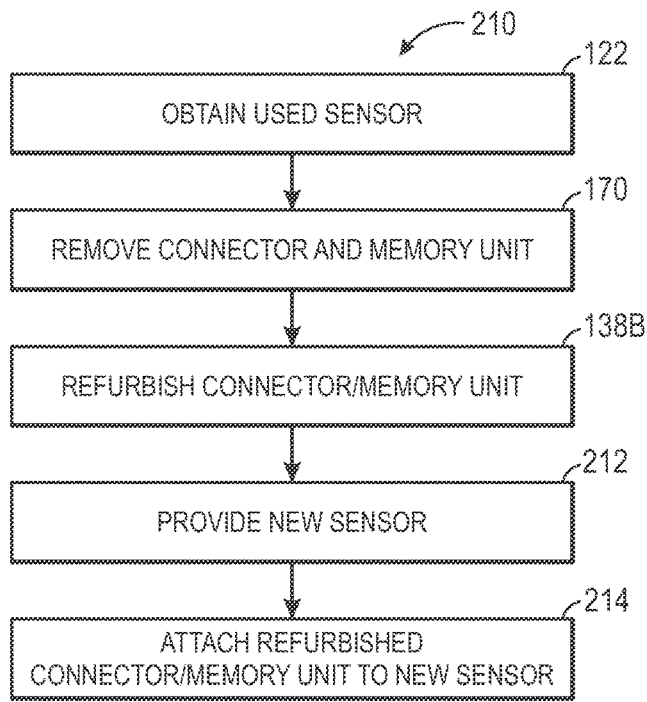
FIG. 13 is a process flow diagram of an embodiment of a method for remanufacturing the sensor of FIG. 1 including retaining only the connector and memory unit and replacing the used sensor with a new sensor, in accordance with an aspect of the present disclosure.

Again, the connector 28 and memory unit 32 may represent a considerable amount of the total cost of the sensors described herein. Indeed, while it may be cost-effective to remanufacture various portions of the sensor 12 including the flexible circuit 50 and foam layers 58, 60, 62 of FIG. 2, it may be desirable to incorporate the used memory unit 32 and, in some embodiments, the connector 28, into a new sensor, such as the sensor 12 or another type of sensor. With this in mind, FIG. 13 illustrates an embodiment of a method 210 for integrating a used connector 28 and associated memory unit 32 with a new sensor.

Method 210 includes obtaining the used version of the sensor 12 (block 122) as described above with respect to FIGS. 3-6. For example, the sensor 12 may be obtained after the sensing and memory components have been tested (e.g., from a testing facility), after the sensor 12 has been sterilized (e.g., from a sterilization facility), or after the sensor 12 has been used to monitor a patient (e.g., from a medical facility). The connector 28 and memory unit 32 may then be removed (block 170) as described above with respect to FIG. 8. For example, the connector 28 having the memory unit 32 may be removed from the sensor cable or the connector 28 having the memory unit 32 and at least a portion of the sensor cable may be removed from the sensor 12.

Before or after removal of the connector 28 from the sensor 12, the memory unit 32 may be remanufactured according to method 138B described above with respect to FIG. 9, which includes re-programming the used memory unit 32. A new sensor may also be provided (block 212), such as a sensor having new electrical components and new layers disposed about the electrical components (e.g., flexible circuit 50 including emitter 16 and detectors 18 of FIG. 2). It may be appreciated that in embodiments where the memory unit 32 is remanufactured after being removed from the connector 28, that the new sensor may also include a new connector 28. The remanufactured memory unit 32, or remanufactured memory unit 32 and connector 28, may then be attached to the new sensor (block 214).

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims.

What is claimed is:

1. A remanufactured medical sensor, comprising:
a padding layer;
a flexible circuit secured to the padding layer and comprising a plurality of conductors disposed on a flexible substrate;
an emitter electrically coupled to the flexible circuit and adapted to transmit light into a patient tissue;
a first detector coupled to the flexible circuit and configured to detect a first portion of light passing through the patient tissue;
a second detector coupled to the flexible circuit and configured to detect a second portion of light passing through the patient tissue; and
a patient-contacting adhesive layer configured to secure the remanufactured medical sensor to the patient tissue;
wherein the padding layer is a trimmed padding layer from a used medical sensor, and wherein the patient-contacting adhesive layer is a new patient-contacting adhesive layer that is disposed directly on a used patient-contacting adhesive layer of the used medical sensor, and wherein the used patient-contacting adhesive layer is trimmed such that a perimeter of the used patient-contacting adhesive layer fits within extents of the new patient-contacting adhesive layer.

2. The remanufactured medical sensor of claim 1, wherein the flexible circuit tapers at one end into a first sensor cable, and the first sensor cable is coupled to a second sensor cable comprising one or more conductors disposed within an insulating material.

3. The remanufactured medical sensor of claim 1, wherein the flexible circuit is coupled to a sensor cable comprising one or more conductors disposed within an insulating material, and the sensor cable is coupled to a connector comprising a memory unit, wherein the connector is adapted to couple the remanufactured medical sensor to a patient monitor.

4. The remanufactured medical sensor of claim 3, wherein the connector, the memory unit, the sensor cable, or any combination thereof, are from the used medical sensor.

5. The remanufactured medical sensor of claim 3, wherein the memory unit is from the used medical sensor and has been re-programmed to enable continued operation of the emitter, the first detector, and the second detector.

6. The remanufactured medical sensor of claim 3, wherein the memory unit comprises an erasable programmable read-only memory (EPROM) unit.

7. The remanufactured medical sensor of claim 3, wherein the memory unit is a replacement memory unit configured to emulate an original memory unit of the used medical sensor.

8. The remanufactured medical sensor of claim 1, comprising an inner foam layer secured to the flexible circuit and the patient-contacting adhesive layer, wherein the flexible circuit is disposed between the inner foam layer and the padding layer, the padding layer comprises an exterior foam layer, the inner foam layer comprises first, second, and third optical windows corresponding to the position of the emitter, the first detector, and the second detector, respectively.

9. The remanufactured medical sensor of claim 1, wherein the patient-contacting adhesive layer is laminated over a used patient-contacting adhesive layer.

10. The remanufactured medical sensor of claim 1, wherein the patient-contacting adhesive layer covers the emitter and the first and second detectors, and is transparent with respect to the wavelengths of light transmitted through the patient tissue.

11. The remanufactured medical sensor of claim 1, wherein the patient-contacting adhesive layer comprises first, second, and third windows corresponding to the emitter and the first and second detectors, respectively.

12. The remanufactured medical sensor of claim 1, wherein the medical sensor comprises a regional oximeter.

13. A patient monitoring system, comprising:
a remanufactured regional oximetry sensor, comprising:
  a padding layer;
  a flexible circuit secured to the padding layer and comprising a plurality of conductors disposed on a flexible substrate;
  an emitter electrically coupled to the flexible circuit and adapted to transmit light into a patient tissue;
  a first detector coupled to the flexible circuit and configured to detect a first portion of light passing through the patient tissue;
  a second detector coupled to the flexible circuit and configured to detect a second portion of light passing through the patient tissue;
  a patient-contacting adhesive layer configured to secure the remanufactured regional oximetry sensor to the patient tissue, wherein the padding layer is a trimmed padding layer from a used regional oximetry sensor, wherein the patient-contacting adhesive layer is a new patient-contacting adhesive layer that is disposed directly on a used patient-contacting adhesive layer of the used regional oximetry sensor, and wherein the used patient-contacting adhesive layer is trimmed such that a perimeter of the used patient-contacting adhesive layer fits within extents of the new patient-contacting adhesive layer; and
a patient monitor adapted to couple with a connector of the remanufactured regional oximetry sensor and operable to monitor signals indicative of the first portion of light received by the first detector and the second portion of light received by the second detector to estimate a blood oxygen saturation level of hemoglobin in a region underlying the patient tissue.

14. The patient monitoring system of claim 13, wherein the remanufactured regional oximetry sensor comprises a sensor cable coupling the flexible circuit with the connector comprising a memory unit, wherein the connector, the memory unit, the sensor cable, or any combination thereof, are from the used regional oximetry sensor.

15. A remanufactured medical sensor, comprising:
a padding layer;
a flexible circuit secured to the padding layer and comprising a plurality of conductors disposed on a flexible substrate;
an emitter electrically coupled to the flexible circuit and adapted to transmit light into a patient tissue;
a first detector coupled to the flexible circuit and configured to detect a first portion of light passing through the patient tissue;
a second detector coupled to the flexible circuit and configured to detect a second portion of light passing through the patient tissue; and
a patient-contacting adhesive layer configured to secure the remanufactured medical sensor to the patient tissue;
wherein the padding layer is a trimmed padding layer from a used medical sensor, wherein the trimmed padding layer comprises a used interior foam layer with a portion of the used interior foam layer trimmed away, and wherein the patient-contacting adhesive layer is a new patient-contacting adhesive layer that is disposed on an additional foam layer secured directly to the trimmed padding layer.

* * * * *